United States Patent
Nag et al.

(10) Patent No.: US 6,448,450 B1
(45) Date of Patent: Sep. 10, 2002

(54) 1-(3,5-DIMETHOXYPHENYL)-2-(4-HYDROXYPHENYL)-ETHYLENE FOR DIABETES TREATMENT

(75) Inventors: Bishwajit Nag, Fremont; Satyanarayana Medicherla, Sunnyvale, both of CA (US); Jai P. Chansouria; Anil B. Ray, both of Varanasi (IN)

(73) Assignee: Calyx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/075,355

(22) Filed: May 8, 1998

(51) Int. Cl.$^7$ ................................................ C07C 41/00
(52) U.S. Cl. ....................................... 568/646; 514/720
(58) Field of Search ........................... 568/646; 514/720

(56) References Cited

U.S. PATENT DOCUMENTS

| | | | | |
|---|---|---|---|---|
| 2,496,968 A | * | 2/1950 | Walton | 260/613 |
| 4,996,237 A | * | 2/1991 | Pettit | 514/720 |
| 5,430,062 A | * | 7/1995 | Cushman | 514/646 |
| 5,547,983 A | * | 8/1996 | Charpentier | 514/535 |
| 5,569,786 A | * | 10/1996 | Pettit | 568/646 |
| 5,886,029 A | * | 3/1999 | Dhaliwal | 514/456 |

OTHER PUBLICATIONS

Chakravarthy et al., "The Prophylactic Action of (−)-Epicatechin Against Alloxan Induced Diabetes in Rats," *Life Science*, vol.29, pp. 2043–2047, 1981.

Farbooniay et al., "Antihyperlipidemic Effect of Flavonoids from Pterocarpus Marsupium," *Journal of Natural Products*, vol. 56, No. 7, pp. 989–994, Jul. 1993.

Manickam et al., "Antihyperglycemic Activity of Phenolics from *Pterocarpus marsupium* ," *Journal of Natural Products*, vol. 60, No. 6, pp. 609–610.

Maurya et al., "Marsupsin, A New Benzofuranone from Pterocarpus Marsupium Roxb.," *Heterocycles*, vol. 19, No. 11, pp. 2103–2107, 1982.

Maurya et al., "Constituents of Pterocarpus Marsupium," *Journal of Natural Products*, vol. 47, No. 1, pp. 179–181, Apr. 1983.

Sheehan et al., "A Constituent of Pterocarpus Marsupium, (−)-Epicatechin, As a Potential Antidiabetic Agent," *Journal of Natural Products*, vol. 46, No. 2, pp. 232–234, 1983.

* cited by examiner

Primary Examiner—Michael L. Shippen
(74) Attorney, Agent, or Firm—Pillsbury Winthrop LLP

(57) ABSTRACT

A diphenylethylene *Pterocarpus marsupium* is provided which is administered orally to decrease blood glucose levels in rats. The compound is an effective anti-diabetic agent that can reduce abnormality of glucose metabolism in diabetes.

1 Claim, 2 Drawing Sheets

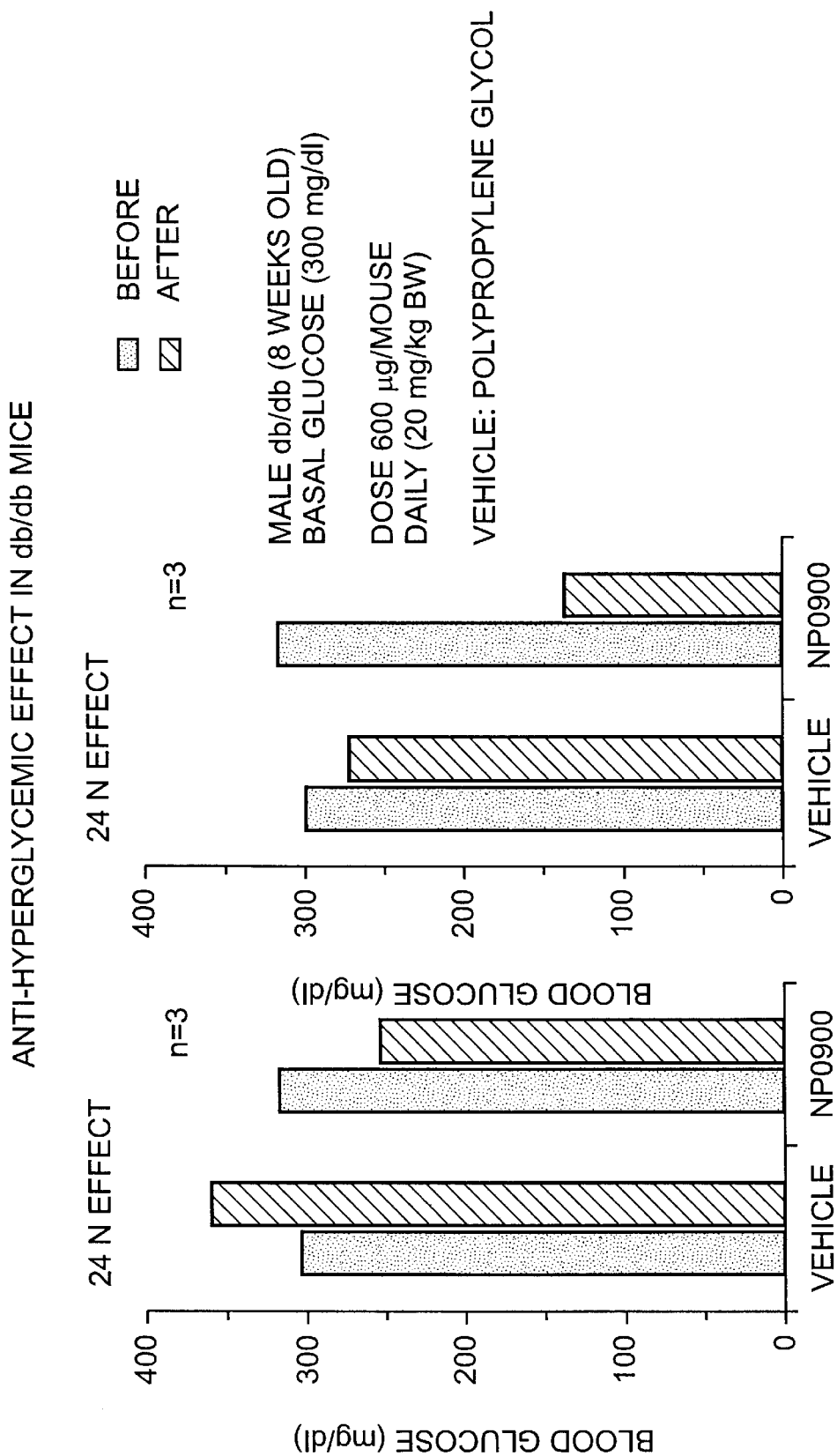

1-(3,5-DIMETHOXYPHENYL)-2-(4-HYDROXYPHENYL)-ETHYLENE FOR DIABETES TREATMENT

FIELD OF THE INVENTION

The field of the invention is a diphenylethylene derivative and its use for treatment of diabetes.

BACKGROUND OF THE INVENTION

Extracts of the leaves, flowers, and gum of the tree *Pterocarpus marsupium* Roxb. (Leguminosae), also known as the Indian Kino Tree, have been used traditionally for the treatment of diarrhea, toothaches, fever and urinary and skin infections. Extracts of the bark have been long regarded as useful for the therapy of diabetes. Hypoglycemic activity of a naturally occurring pterostilbene, 3,5-dimethoxy-4'-hydroxy-trans-stilbene, isolated from the heartwood of pterocarpus marsupium as been reported by Manickam et al., *J. Nat. Prod.*, 1997, 60:609–610. However, this pterostilbene is water insoluble and has not been shown to be efficacious in the treatment of diabetes, particularly in instances where insulin is present but inactive. The cause of diabetes is yet unknown, although both genetics and environment appear to be factors. Insulin dependent (Type I) and non-insulin dependent (Type II) are the types of diabetes. Type I is an autonomic immune disease in which the responsible autoantigen is still unknown. Patients of Type I need to take insulin intravenously to survive. However, Type II diabetes, the more common form of the disease, is a metabolic disorder resulting from the body's inability to make a sufficient amount of insulin or to properly use the insulin that is produced within the body. Insulin secretion and insulin resistance are considered the major defects, however, the precise genetic factors involved in the mechanism remain unknown.

Patients with diabetes usually have one or more of the following defects: less production of insulin by the pancreas; over secretion of glucose by the liver; impairment of glucose uptake by the skeletal muscle; defects in glucose transporters; desensitation of insulin receptors; and defects in the metabolic breakdown of polysaccharides. Other than the intravenous application of insulin, there are four classes of oral hypoglycemic agents in use.

| Class | Approved Drugs | Mechanisms of Action | Limitations |
|---|---|---|---|
| sulfur urea | 4 (1st generation) and 2 (2nd generation) | acts on pancreas to release more insulin | dev. of resistance |
| biguanides | metformin | reduces glucose secretion by liver; improves insulin sensitivity | liver problems, lactic acidosis |
| alpha-glucosidase inhibitor | acarbose | interferes with digestive process; reduces glucose absorption | only useful at post-pradiandio level |
| thiazolidine-dione | troglipzone | reduces insulin resistancy | "add-on" with insulin; not useful for people with heart and liver disease |

As is apparent from the above table, each of the current agents available for use and treatment of diabetes has certain disadvantages. Accordingly, there is a continuing interest in the identification and development of new agents, particularly, water soluble agents which can be orally administered, for the use of treatment of diabetes.

Besides the pterostilbene discussed above, (−)-epicatechin, has also been isolated from pterocarpus marsupium by Sheehan et al., *J. Nat. Prod.*, 1983, 46:232, and has been reported as having a hypoglycemic effect. See also Chakravarthy et al., *Life Sciences*, 1981, 29:2043–2047. Other phenolic type compounds have been isolated from pterocarpus marsupium by Maurya et al., *J. Nat. Prod.*, 1984, 47:179–181; Jahromi et al., *J. Nat. Prod.*, 1993, 56:989–994; and Maurya et al., *Heterocycles*, 1982, 19:2103–2107.

SUMMARY OF THE INVENTION

A diphenylethylene is provided having the following formula I.

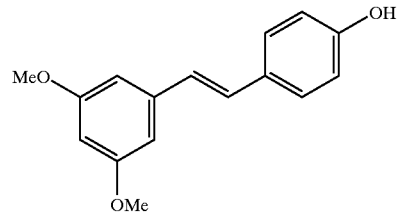

Pharmaceutical compositions containing the compound of the formula I are provided for treatment of diabetes comprising of therapeutically effective amount of the compound in a physiologically acceptable carrier.

A method of treating diabetes is also provided comprising the step of orally administering to a subject suffering from a diabetic condition a therapeutically effective amount of a compound of formula I.

BRIEF DESCRIPTION OF THE DRAWINGS

FIGS. 2A and 2B shows the blood glucose levels at one hour and twenty-four hours, respectively, after treatment of diabetic mice with the diphenylethylene.

DESCRIPTION OF THE PREFERRED EMBODIMENTS

Figure 1:
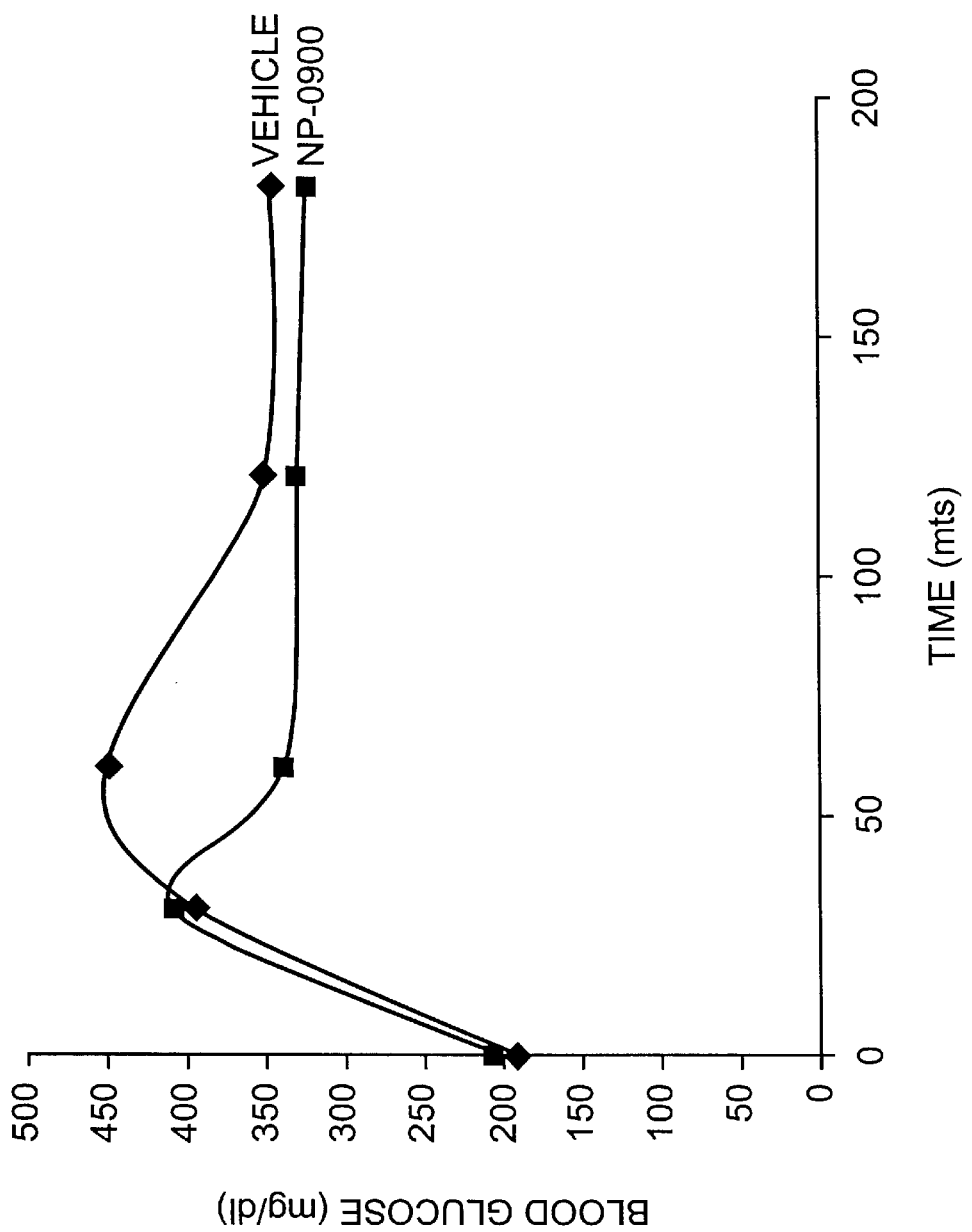
FIG. 1 shows the effect of the diphenylethylene on blood glucose levels in STZ induced diabetic rats.

The diphenylethylene is prepared by condensation of 3,5-dimethoxybenzaldehyde and p-hydroxyphenyl acetic acid, followed by decarboxylation.

The diphenylethylene compound according to the present invention may be combined with a physiologically acceptable vehicle in pharmaceutical composition, such as, a lyophilized powder in the form of tablets or capsules which also includes various fillers and binders. The effective dosages of the compound in a composition will be selected by those of ordinary skill in the art and may empirically be determined.

The compound of the present invention are useful for the treatment of diseases such as diabetes characterized by the presence of elevated blood glucose levels, that is, hyperglycemic disorders such as diabetes melitus, including both Type I and II diabetes as well as other hyperglycemic related disorders such as obesity, increased cholesterol, kidney related disorders, and the like.

By "treatment", it is meant that the compound is administered at least to reduce the blood glucose level in the patient suffering from the hyperglycemic disorder. The compound is administered in an amount sufficient to reduce blood glucose level to an acceptable range, wherein an acceptable range means ±10%, usually ±8% and usually ±5% of the normal average blood glucose level for the subject. A variety of subjects may be treated with the compounds to reduce blood glucose levels, such as livestock, valuable or rare animals, pets, as well as humans. The compound may be administered to the subject suffering from the hyperglycemic disorder using a convenient administration technique, including intravenous, intradermal, intramuscular subcutaneous, oral and the like. The dosage delivered to the host will necessarily depend upon the route by which the compound is delivered, but generally ranges from 5 to 500 mg/70 kg human body weight or typically from about 50 to 200 mg/70 kg human body weight.

Of particular interest are methods of treating human hyperglycemic disorder such as diabetes, including both Type I and II, where the compound is administered to the human suffering from the hyperglycemic disorder to at least reduce the blood glucose level of the subject to about the normal blood glucose range for a human.

The following examples are offered by way of illustration and not intended to limit the invention in any way.

EXAMPLE 1

Preparation of 1-(3,5-dimethoxyphenyl)-2-(4-hydroxyphenyl)ethylene

To a mixture of 3,5-dimethoxybenzaldehyde (30 mM) and p-hydroxphenyl acetic acid (30 mM) was added to 5 mL acetic anhydride and 2.5 mL of triethylamine (TEA). After being stirred at 130–140° C. for 24 hr, the mixture was cooled to room temperature and quenched with 25 mL concentrated HCl and extracted with $CH_2Cl_2$. The organic extract was further extracted with IN NaOH, then the NaOH extract was washed with water, the aqueous layer was acidified with conc. HCl and washed with water to obtain the crude product. Crude product was recrystallized from ethanol/water. To 1 g of this product under $N_2$, 3 g of Cu power and 30 mL of quinoline was added, the mixture was refluxing with stirring for 4 hr. The reaction mixture was filtered, diluted with water and extracted with $CH_2Cl_2$. Organic layer was dried and concentrated, product was purified by flash chromatography.

EXAMPLE 2

Streptozotocin (STZ) induced diabetic rats were made by injecting STZ (40 mg/kg/bw) intravenously. Following verification of blood glucose levels after 72 hours, diabetic rats showing fasting blood glucose levels above 200 mg/dl were divided into two groups. The diphenylethylene was administered to one group in a dose of 20 mg/kg/bw in propyleneglycol. The control group received only propyleneglycol. Soon after the administration of the compound, glucose tolerance testing was conducted by a glucose load of 2 g/kg/bw and blood glucose levels were monitored at zero, 30, 60, 120 and 180 minutes by milking the tail of the rats. The results are shown in FIG. 1. In the group treated with the pterostilbene it can be seen that after about 30 minutes, the blood glucose levels begin to fall and stayed consistently below the blood glucose levels in the control group until the end of the test.

EXAMPLE 3

The same test was conducted on STZ induced diabetic rats comparing the diphenylethylene with the commercial product metformin. The diphenylethylene was administered at a dose of 20 mg/kg and metformin was administered at the dosage of 30 mg/kg. The results are shown below in Table 1.

TABLE 1

EFFECT ON STREPTOZOTOCIN-INDUCED DIABETIC RATS

|  | BEFORE | AFTER | % CHANGE |
| --- | --- | --- | --- |
| Vehicle | 326 ± 5 | 325 ± 5 |  |
| Pter. (20 mg/kg) | 377 ± 37 | 219 ± 48 | −42 |
| Metformin (30 mg/kg) | 358 ± 24 | 188 ± 36 | −48 |

Journal of Natural Products (1997) 60, 609–610.

It can be seen by the glucose levels obtained by the administration of the diphenylethylene are equivalent to those obtained by the commercial product.

EXAMPLE 4

Six spontaneously diabetic (db/db) mice were divided into two groups of three each. One test group receives the diphenylethylene (20 mg/kg/bw/ip) in propyleneglycol. The control group received an equal volume of propyleneglycol. Soon after the administration of the test materials, blood glucose levels were monitored at 1 hour (see FIG. 2A) and 24 hours (see FIG. 2B) after treatment. The diphenylethylene reduced the blood glucose level by over 50 percent within 24 hours, thus establishing its antihyperglycemic effect.

What is claimed is:

1. A method of treating diabetes comprising the step of administering to a subject suffering from a diabetic condition a therapeutically effective amount of a synthesized substantially pure compound of the formula I:

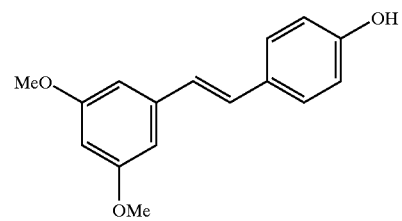

in a physiologically acceptable carrier, the treatment being sufficient to reduce the blood glucose level to ±10% of the normal average blood glucose level for the subject.

* * * * *